United States Patent [19]

Stendel et al.

[11] Patent Number: 5,266,324
[45] Date of Patent: Nov. 30, 1993

[54] PROCESSES AND AGENTS FOR COMBATING FLEAS

[75] Inventors: Wilhelm Stendel, Wuppertal; Reiner Pospischil, Bergheim; Herbert Voege, Leverkusen, all of Fed. Rep. of Germany

[73] Assignee: Bayer Aktiengesellschaft, Leverkusen, Fed. Rep. of Germany

[21] Appl. No.: 913,771

[22] Filed: Jul. 14, 1992

Related U.S. Application Data

[63] Continuation of Ser. No. 739,061, Aug. 1, 1991, abandoned.

[30] Foreign Application Priority Data

Aug. 10, 1990 [DE] Fed. Rep. of Germany ....... 4025345

[51] Int. Cl.⁵ .................. A01N 25/34; A01N 31/14
[52] U.S. Cl. .................. 424/411; 424/405; 514/876; 514/327
[58] Field of Search .......... 424/411, 84, DIG. 10; 514/919, 964, 876

[56] References Cited

U.S. PATENT DOCUMENTS

| | | | |
|---|---|---|---|
| 4,160,335 | 7/1979 | Von Kohorn et al. | 43/131 |
| 4,879,117 | 11/1989 | Rombi | 424/411 |
| 4,997,650 | 3/1991 | Kamada et al. | 424/409 |

FOREIGN PATENT DOCUMENTS 0124404 11/1984 European Pat. Off. .
0339821 10/1989 European Pat. Off. .

OTHER PUBLICATIONS

Chem Abstracts, 1990-113:58946f.
Chem Abstracts, 1985-103:49777t.
Database WPIL Derwent Pub. JP-A-59008956 (Jan1094).

*Primary Examiner*—Thurman K. Page
*Assistant Examiner*—Neil Levy
*Attorney, Agent, or Firm*—Sprung Horn Kramer et al.

[57] ABSTRACT

The present invention relates to processes and agents for combating fleas on, and in the surroundings of, domestic animals, which is characterised in that the domestic animals are treated with collars which contain active compounds which inhibit insect development.

7 Claims, No Drawings

PROCESSES AND AGENTS FOR COMBATING FLEAS

This application is a continuation of application Ser. No. 739,061, filed Aug. 1, 1991, now abandoned.

The present invention relates to processes and agents for combating fleas on, and in the surroundings of, domestic animals, which contain substances which inhibit insect development.

Adult fleas usually live preferably in the coat of their host animals. They feed on the latter's blood and lay their eggs in the coat of the particular host animal.

Since the eggs deposited do not adhere to the coat of the host, they fall off rapidly and can therefore be found above all in the surroundings of the host animals, for example in their beds and bedding.

This means that preferably beds and bedding of the host animals are infested with flea eggs, from which flea larvae hatch within a few days. Three developmental stages can be distinguished in the larvae, each of which lasts approximately 3 days. The third larval stage spins a cocoon and pupates. Under favourable conditions (20°–30° C., 60–80% relative humidity), the development from the egg to the pupa lasts approximately 10 days. After about 8 more days, development of the fleas is complete, and fleas which are ready to hatch can be found in the cocoons lying on the floor (carpets, sleeping places etc.). The young flea can remain in its cocoon for months.

Under unfavourable conditions, however, the development from the egg to the adult young flea can last as long as 4–5 months. In order to reach sexual maturity, that is to say to lay fertile eggs, fleas require blood as food. Ideally, this blood is from the particular specific host. However, particularly after a relatively long fasting period, fleas can also accept the blood of other hosts.

Infestation by fleas of domestic animals such as dogs and cats is not only a nuisance for the infested animal, but also causes considerable pain (injuries by biting, itching and allergies) and harm (loss of blood) to the infested animals. Fleas can also pass on various species of tapeworm. They therefore also represent a medical problem for the infested animals and for the animal owners. However, it is also possible for the animal owner to be bitten by fleas. In some humans, this causes allergy to flea bites. For this reason, effective control of fleas in dogs and cats has always been desirable and necessary, especially since these domestic animals live in an increasingly greater number and in increasingly close contact with man.

A large number of insecticidal active compounds has been disclosed to date for combating fleas. Examples of such active compounds are, from the class of the carbamates propoxur, bendiocarb and carbaryl, from the class of the phosphates fenthion and diazinone, and from the class of the pyrethroids permethrin, cypermethrin and resmethrin.

These active compounds are contact insecticides which act mainly on adult fleas. These active compounds have no effect on eggs or on the pupated stages of the fleas.

The active compounds are used on the host animal, and applied, for example by spraying, douching, washing, as a powder, or by pouring-on or spotting-on. They can also be incorporated into collars. The active compounds are also used in the immediate or further surroundings of the host animals in the form of aerosols, spray formulations and dusts. For this purpose, beds and the home and areas outside the home are treated.

It is also known that insect development inhibitors such as methoprene or cyromazine can be added to the agents with which the surroundings of the host animals are treated. This stops the development of adult fleas from eggs and larvae and pupae. However, to date it was necessary for the entire surroundings of the host animals, that is to say the entire home of the human, to be treated.

It is also known that reinfestation of dogs and cats by fleas can be prevented by treating dogs and cats orally or parenterally with active compounds which inhibit the growth of fleas (EP-OS (European Published Specification) 255,803).

It is furthermore known that dogs and cats can be protected against fleas by spraying with an aerosol formulation containing methoprene. In doing so, it was possible to prevent flea larvae developing from the deposited eggs (International Pest Control 27, 1985, pp. 10–14).

There are also known animal collars which have been impregnated with a solution containing methoprene (EP-OS (European Published Specification) 124,404).

All insecticide-based or insect-development-inhibitor-based methods which are known to date for combating fleas in domestic animals involve treatment of the host animal (dog or cat), its bedding or its entire surroundings. Treatment of the host animals alone is of little promise since for weeks and even months there is the risk of reinfestation by freshly hatched fleas from the surroundings. Treatment of only the bedding of the host animal is also of little promise since the animals change their beds, and some beds are not even known or (in particular in the case of cats) are not accessible for treatment.

The greatest success can therefore be achieved when the host animals as well as their entire surroundings are treated. Treatment of the surroundings is labour-intensive and requires plenty of material. Possibilities should therefore be sought which reduce the amount of labour and the material employed for the treatment.

This is made possible by the present invention.

It has been found that fleas on, and in the surroundings of, domestic animals can be combated by treating the domestic animals with collars which contain insect-development inhibitors.

New animal collars have been found which contain insect-development inhibitors. An exception are collars based on absorptive material which has been impregnated with methoprene.

In this way, the treated animals provide, simultaneously with the distribution of the flea eggs, for a targeted distribution of the active compound to those locations from which a reinfestation with fleas may occur. Hence, the animals themselves provide the targeted distribution of the active compound. In this way, neither are locations left out which must be treated, nor is active compound wasted in locations in which the host animal does not stay. Moreover, the labour in connection with the application of the active compound is dispensed with.

It was surprising that an effect could be achieved by this way of applying the active compound. In the methods known to date, the eggs or larvae in the surroundings were treated directly or came into contact with the active compound on the animals when the latter were treated.

However, it could not have been expected that efficient control of fleas in the surroundings is possible by the treatment according to the invention.

The success of the treatment can even be increased by adding, to the collars, an insecticide which is active against fleas (adulticide) for combating the adult fleas.

Domestic animals which may be mentioned are dogs and cats. The following may be mentioned as fleas: Ctenocep halides spec., Pulx spec., Xenopsylla spec., Ceratophyllus spec., Echidnophaga spec., Tunga spec.

The following may be mentioned as active compounds which have an insect-development-inhibiting action: juvenile hormones or juvenile-hormone-type substances, substituted diaryl ethers, benzoylureas and triazine derivatives. These compounds are known. The juvenile hormones and juvenile-hormone-type substances include, in particular, compounds of the following formulae:

$NO_2$, alkenyl, alkinyl, alkoxyalkyl, alkoxyalkoxy or hydroxyalkoxy, $R^2$ represents the radicals mentioned under $R^1$, $R^3$ represents the radicals mentioned under $R^1$, $R^4$ represents hydrogen, alkyl, halogenoalkyl or halogen, $R^5$ represents the radicals mentioned under $R^4$, Het represents optionally substituted heteroaryl which is not bonded to the remaining radical via the heteroatom, X and Y independently of one another represent —O— or —S—, Z represents —O—, —S—, —$CH_2$—, —$CHCH_3$—, —$C(CH_3)_2$—, m and n independently of one another represent 0, 1, 2 or 3, but their total is equal to, or greater than, 2.

Preferred compounds of the formula I are those in which $R^1$ represents hydrogen, fluorine, chlorine, bromine, $C_{1-4}$-alkyl, $C_{1-4}$-alkoxy, $C_{1-4}$-alkylthio, $C_{1-4}$-halogenoal-

[Chemical structures shown]

The substituted diaryl ethers include, in particular, substituted alkoxydiphenyl ethers or -diphenylmethanes of the general formula I

[Structure of formula I showing diphenyl ether with R¹, R², R³, R⁴, R⁵ substituents and Y—(CH)ₙ—(CH)ₘ—X—Het chain, with Z linkage]

where $R^1$ represents hydrogen, halogen, alkyl, alkoxy, alkylthio, halogenoalkyl, halogenoalkoxy, halogenoalkylthio, dioxyalkylene, dioxyhalogenoalkylene, CN, kyl having up to 5 halogen atoms, in particular trichloromethyl, trifluoromethyl, $C_{1-4}$-halogenoalkoxy having up to 5 halogen atoms, in particular trichloromethoxy, trifluoromethoxy, $C_{1-4}$-halogenoalkylthio having up to 4 halogen atoms, in particular trifluoromethylthio, CN, $NO_2$, $C_{2-3}$-alkenyl, $C_{1-4}$-alkoxy-$C_{1-2}$-alkyl, in particular ethoxymethyl, methoxyethyl, $C_{1-2}$-alkoxy-$C_{1-4}$-alkoxy, in particular methoxyethoxy, $C_{1-4}$-hydroxyalkoxy, in particular hydroxyethoxy, dioxyethylene, dioxymethylene, difluorodioxymethylene, trifluorodioxyethyl-ene or dichlorooxymethylene, $R^2$ represents the radicals mentioned under $R^1$, $R^3$ represents the radicals mentioned under $R^1$, $R^4$ represents hydrogen, $C_{1-4}$-alkyl, $C_{1-4}$-halogenoalkyl having up to 5 halogen atoms, chlorine, fluorine or bromine, R⁵ represents the radicals mentioned under R⁴, Het represents pyridyl, pyridazinyl, pyrimidinyl, or pyrazinyl, each of which is optionally substituted by one or more identical or different radicals from the group comprising $C_{1-4}$-alkyl, such as methyl, ethyl, t-butyl, halogen, such as fluorine, chlorine, bromine, $NO_2$, $C_{1-4}$-alkoxy, $C_{1-4}$-alkylthio, $C_{1-4}$-alkoxy, $C_{1-4}$-alkylthio, $C_{1-4}$-halogenoalkyl having up to 5 halogen atoms, $C_{1-4}$-halogenoalkoxy having up to 5 halogen atoms or $C_{1-4}$-halogenoalkylthio having up to 5 halogen atoms, X and Y independently of one another represent —O— or —S—, Z represents —O—, —S—, —CH₂—, —CHCH₃—, —C(CH₃)₂—, m represents 1 or 2, and n represents 1 or 2.

Particularly preferred compounds of the formula I are those in which $R^1$ represents hydrogen, methyl, trifluoromethyl, methoxy, trifluoromethoxy, chlorine or fluorine, $R^2$ represents hydrogen, $R^3$ represents hydrogen, fluorine, chlorine or methyl, $R^4$ represents hydrogen or methyl, $R^5$ represents methyl, ethyl, trifluoromethyl or hydrogen, Het represents pyridyl or pyridazinyl, each of which is optionally substituted by fluorine, chlorine, methyl, $NO_2$, methoxy or methylmercapto.

The following compounds may be mentioned individually:

| $R^1$ | $R^3$ | $R^5$ | $R^6$ | Z |
|---|---|---|---|---|

[structure: $R^1$—phenyl—Z—phenyl($R^3$)—O—CH₂—CH($R^5$)—O—pyridyl($R^6$)]

| $R^1$ | $R^3$ | $R^5$ | $R^6$ | Z |
|---|---|---|---|---|
| H | H | CH₃ | H | O |
| H | H | CH₃ | 2-Cl | O |
| 5-F | H | CH₃ | H | O |
| H | H | CF₃ | H | O |
| H | H | C₂H₅ | H | O |
| H | H | H | H | O |
| H | H | CH₃ | H | CH₂ |
| H | H | CH₃ | H | C(CH₃)₂ |

[structure: $R^1$—phenyl—Z—phenyl($R^3$)—O—CH₂—CH($R^5$)—O—pyridyl($R^6$)]

| $R^1$ | $R^3$ | Z | Het |
|---|---|---|---|
| H | H | CH₃ | H | O |

[structure: $R^1$—phenyl—Z—phenyl($R^3$)—O(CH₂)₃—O—Het]

| H | H | O | pyridyl (2-) |
| H | H | O | pyridyl (3-) |
| H | H | O | pyridazinyl |

The substituted diaryl ethers also include the compounds of the formula II $$R^1\text{—[dibenzofuran with X, }R^2\text{]—}[Y-(CH)_m-(CH)_n]_o-Z-\text{Het} \qquad \text{II}$$

with $R^3$, $R^4$ on the CH groups where

X represents O, S, NH, —CH₂—, —CHCH₃—, —C(CH₃)₂—,

Y represents O or S,

Z represents O or S, $R^1$ represents identical or different radicals from the group comprising hydrogen, halogen, alkyl, alkoxy or halogenoalkyl, $R^2$ represents identical or different radicals from the group comprising hydrogen, halogen, alkyl, alkenyl, halogenoalkyl, alkoxy, alkylthio, halogenoalkoxy or halogenoalkylthio, $R^3$ represents hydrogen, alkyl, halogenoalkyl, alkoxyalkyl, alkenoxyalkyl, alkenyl or alkinyl, $R^4$ represents the radicals mentioned under $R^3$, $R^3$ and $R^4$ together with the adjacent C atoms can represent saturated or unsaturated 5- to 7-membered carbocyclic rings, m represents 1 or 2, n represents 1 or 2, o represents 1, 2 or 3 and Het represents optionally substituted heteroaryl which is not bonded to the remaining radical via the heteroatom.

The following may be mentioned in particular:

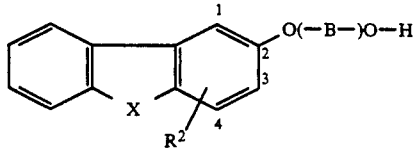
| X | R² | B | Het |
|---|---|---|---|
| O | 1.3 Cl₂ | —CH₂—CH(C₂H₅)— | 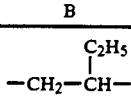 |
| S | H | —CH₂—CH(CF₃)— | 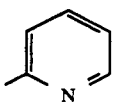 |
| O | 1.3-Cl₂ | —CH₂—CH(CH₂F)— | 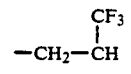 |
| O | 1.3-Cl₂ | —CH₂—CH(CH₂F)— | 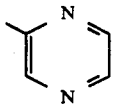 |
| S | 1.3-Cl₂ | —CH₂—CH(CH₂F)— | 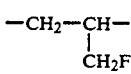 |
| O | 3-Br | —CH₂—CH(CH₂F)— | 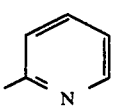 |
| CH₂ | 1.3-Cl₂ | —CH₂—CH(CH₂F)— | 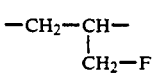 |
| CH₂ | H | —CH₂—CH(CH₂F)— | 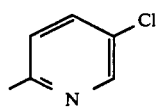 |
| O | H | —CH₂—CH(CH₂F)— | 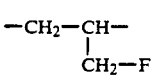 |
| S | H | —CH₂—CH(CH₂F)— | 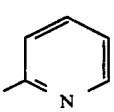 |
| O | 1.3-Cl₂ | —CH₂—CH(CH₂F)— | 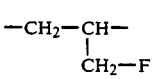 |

-continued
| | | | |
|---|---|---|---|
| O | 1,3-Cl$_2$ | 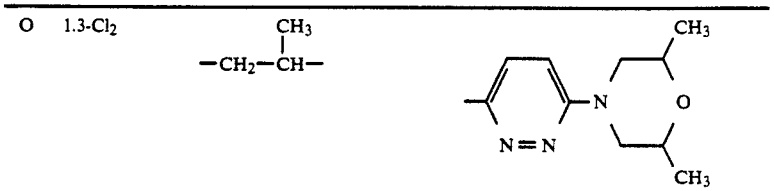 | |
| S | 1,3-Cl$_2$ | 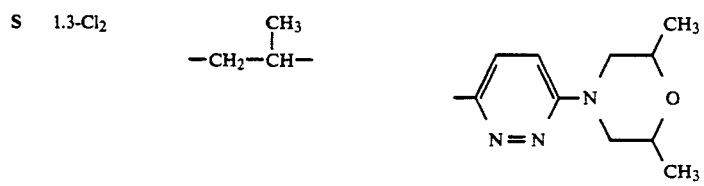 | |
| CH$_2$ | 1,3-Cl$_2$ | 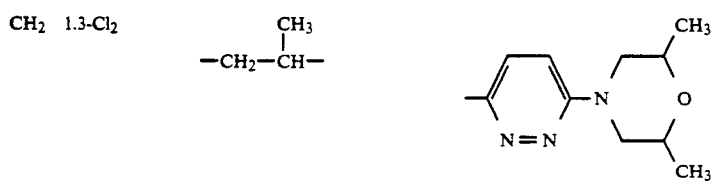 | |
| O | H | 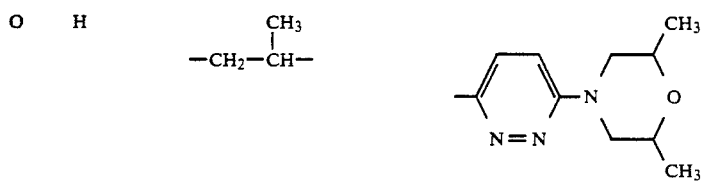 | |
| O | 1,3-Cl$_2$ | 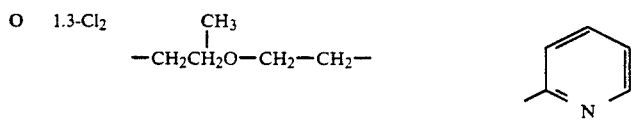 | 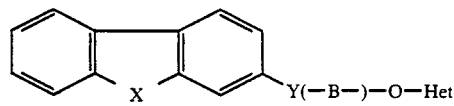 |
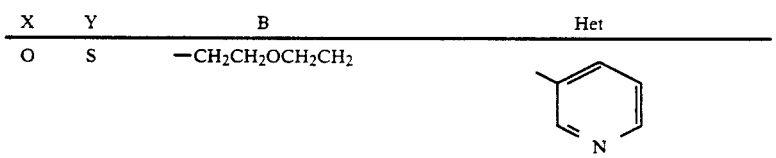
| X | Y | B | Het |
|---|---|---|---|
| O | S | —CH$_2$CH$_2$OCH$_2$CH$_2$— | 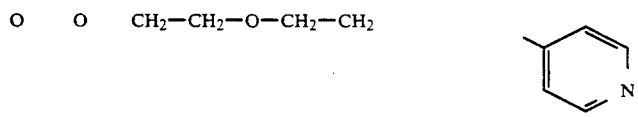 |
| O | O | CH$_2$—CH$_2$—O—CH$_2$—CH$_2$ | 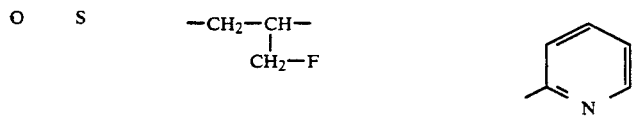 |
| O | S | —CH$_2$—CH— <br>         CH$_2$—F | 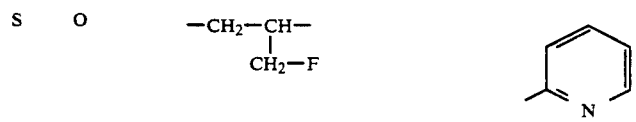 |
| S | O | —CH$_2$—CH— <br>         CH$_2$—F | 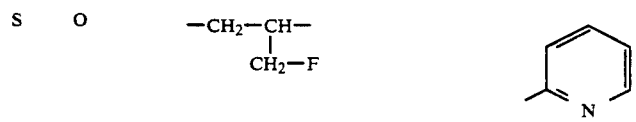 |
| O | O | —CH$_2$—CH— <br>         CH$_2$—F | 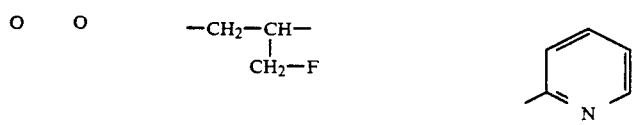 |

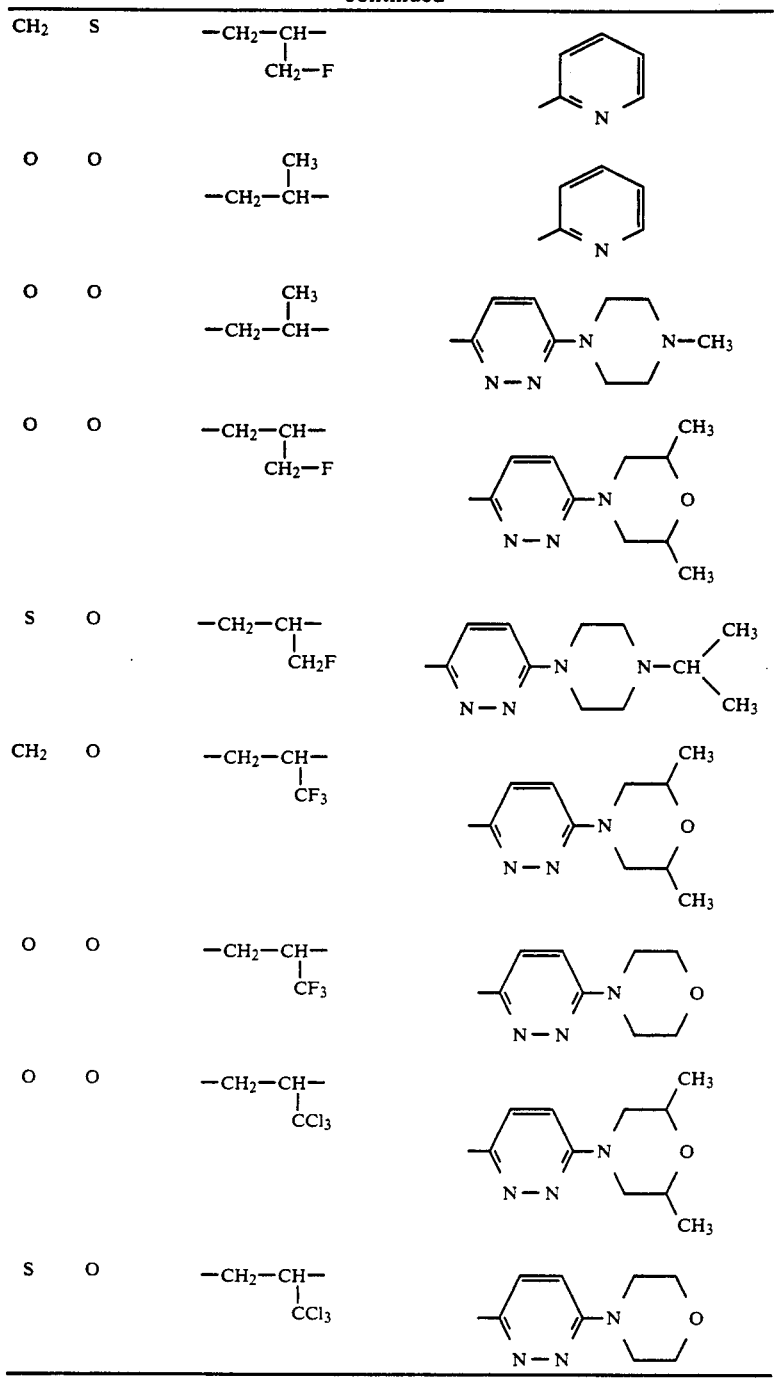
The substituted diaryl ethers furthermore include the compounds of the formula (III)
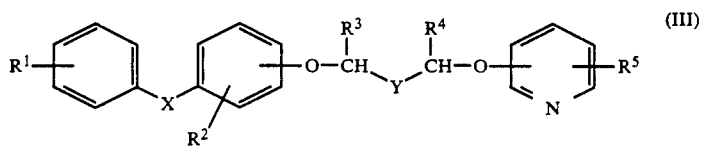
where
X represents O, S, NH, —CH$_2$—, —CHCH$_3$—, —C(CH$_3$)$_2$—,
Y represents straight-chain or branched alkylene which is optionally interrupted by oxygen,
R$^1$ represents identical or different radicals from the group comprising hydrogen, halogen, alkyl, alkoxy and halogenoalkyl, $R^2$ represents identical or different radicals from the group comprising hydrogen, halogen, alkyl, alkenyl, halogenoalkyl, alkoxy, alkylthio, halogenoalkoxy and halogenoalkylthio, $R^3$ represents hydrogen, alkyl, halogenoalkyl, alkoxyalkyl, alkenoxyalkyl, alkenyl or alkinyl, $R^4$ represents the radicals mentioned under $R^3$, $R^3$ and $R^4$ together can represent a direct bond, and $R^5$ represents hydrogen, halogen, alkyl, halogenoalkyl, alkoxy, amino, alkyl, alkylamino, dialkylamino or acylamino.

The following may be mentioned in particular:

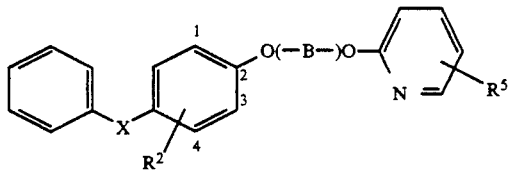

| X | $R^2$ | B | $R^5$ |
|---|---|---|---|
| O | 1.3 Cl$_2$ | —CH$_2$—CH$_2$—O—CH$_2$—CH(CH$_3$)— | 3-NH$_2$ |
| S | H | —CH$_2$—CH(CH$_3$)—O—CH$_2$—CH(CH$_3$)— | 5-N-morpholino |
| O | 1.3-Cl$_2$ | —CH$_2$—CH$_2$—O—CH$_2$CH$_2$— | 4-NH$_2$ |
| O | 1.3-Cl$_2$ | —CH$_2$—CH$_2$—O—CH$_2$CH$_2$— | 3-OCH$_3$ |
| S | 1.3-Cl$_2$ | —CH$_2$—CH$_2$—O—CH$_2$CH$_2$— | 5-OCH$_3$ |
| O | 3-Br | —CH$_2$—CH$_2$—O—CH$_2$CH$_2$— | 5-OCH$_3$ |
| CH$_2$ | 1.3-Cl$_2$ | —CH$_2$—CH$_2$—O—CH$_2$CH$_2$—O—CH$_2$CH$_2$— | 3-NH$_2$ |
| CH$_2$ | H | —CH$_2$—CH$_2$—O—CH$_2$—CH(CH$_3$) | 5-CF$_3$ |
| O | H | —CH$_2$—CH(CH$_3$)—O—CH$_2$—CH(CF$_3$)— | 5-N-[2,6-dimethylmorpholino] |
| S | H | —CH$_2$—CH(CH$_2$F)—O—CH$_2$—CH$_2$— | 5-N-(4-methylpiperazino) |
| O | 1.3-Cl$_2$ | —CH$_2$—CH$_2$—O—CH$_2$CH$_2$— | 3-NH—C(O)—NH—(4-phenoxyphenyl) |
| O | 1.3-Cl$_2$ | —CH$_2$—CH(CH$_3$)—O—CH$_2$CH$_2$— | 5-N-[2,6-dimethylmorpholino] |
| S | 1.3-Cl$_2$ | —CH$_2$—CH(CH$_3$)—O—CH$_2$—CH(CH$_3$)— | 5-N-[2,6-dimethylmorpholino] |

-continued

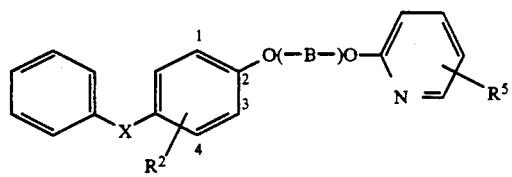

| X | R² | B | R⁵ |
|---|----|----|----|
| CH₂ | 1,3-Cl₂ | —CH₂—CH(CH₃)—O—CH₂CH₂— | 5-N morpholine-2,6-di-CH₃ |
| O | H | —CH₂—CH₂—O—CH₂CH₂— | 5-N morpholine-2,6-di-CH₃ |
| O | 1,3-Cl₂ | —CH₂CH₂O—CH₂—CH₂— | 3-NH—C(=O)—NH—C₆H₄—Cl |
| —CH(CH₃)— | H | —CH₂CH₂—O—CH₂CH₂— | 4-OCH₃ |
| O | H | (5-membered ring) | 3-NH—C(=O)—NH—C₆H₅ |
| O | H | —CH₂CH₂—O—CH₂CH₂CH₂— | 4-NH—C(=O)—NH—C₆H₄—O—C₆H₄—CF₃ |

The diaryl ethers furthermore include the compounds of the formula (IV)

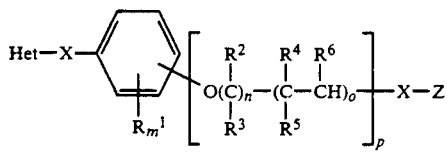

(IV)

in which

Het represents an optionally substituted heteroaromatic radical

X represents O, S, —CH₂—,

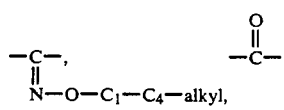

Y represents O, —O—CH₂—, S,

Z represents an optionally substituted aromatic or heteroaromatic radical;

m represents integers from 1 to 4, n represents 0, 1, 2, 3 or 4, o represents 0, 1, 2, 3 or 4, where n and o must not simultaneously represent 0, p represents integers from 1 to 4, R², R³, R⁴, R⁵, R⁶ independently of one another represent hydrogen, $C_1$-$C_6$-alkyl, which is optionally substituted by halogen or $C_{1-4}$-alkoxy; two radicals which are adjacent to each other can also, together with the C atoms to which they are bonded, form a saturated carbocyclic 5- or 6-ring, and R¹ represents identical or different radicals from the group comprising hydrogen, halogen, CN, $C_{1-4}$-alkyl, 1-5-halogeno-$C_{1-4}$-alkyl, $C_{1-4}$-alkoxy, $C_{1-4}$-alkylthio, 1-5-halogeno-$C_{1-4}$-alkoxy, 1-5-halogeno-$C_{1-4}$-alkylthio, phenyl or phenoxy.

The following may be mentioned in particular:

| X | R¹ | B | Het |
|---|---|---|---|

Structure header: pyridine-X-phenyl(R¹ at position 4, positions 1,2,3 labeled)-O(-B-)O-Het

| X | R¹ | B | Het |
|---|---|---|---|
| O | 1.3-Cl₂ | -CH₂-CH(C₂H₅)- | 2-pyridyl |
| S | H | -CH₂-CH(CF₃)- | pyrazinyl |
| O | 1.3-Cl₂ | -CH₂-CH(CH₂F)- | 2-pyridyl |
| O | 1.3-Cl₂ | -CH₂-CH(CH₂F)- | 3-pyridyl |
| S | 1.3-Cl₂ | -CH₂-CH(CH₂F)- | 2-pyridyl |
| CH₂ | 1.3-Cl₂ | -CH₂-CH(CH₂F)- | 2-pyridyl |
| CH₂ | H | -CH₂-CH(CH₂F)- | 2-pyridyl |
| O | H | -CH₂-CH(CH₂F)- | 2-pyridyl |
| S | H | -CH₂-CH(CH₂F)- | 2-pyridyl |
| O | 1.3-Cl₂ | -CH₂-CH(CH₂F)- | 4-pyridyl |
| O | 1.3-Cl₂ | -CH₂-CH(CH₃)- | methyl-pyridazinyl substituted with morpholine bearing two CH₃ groups |

-continued

| X | R¹ | B | Het |
|---|---|---|---|
| S | 1.3-Cl₂ | −CH₂−CH(CH₃)− | 6-methyl-3-(2,6-dimethylmorpholin-4-yl)pyridazine |
| CH₂ | 1.3-Cl₂ | −CH₂−CH(CH₃)− | 6-methyl-3-(2,6-dimethylmorpholin-4-yl)pyridazine |
| O | H | −CH₂−CH(CH₃)− | 6-methyl-3-(2,6-dimethylmorpholin-4-yl)pyridazine |
| O | 1.3-Cl₂ | −CH₂CH(CH₃)O−CH₂−CH₂− | 2-pyridyl | dibenzofuran/thiophene skeleton: Y(−B−)−O−Het

| X | R¹ | B | Het |
|---|---|---|---|
| O | S | −CH₂CH₂OCH₂CH₂− | 3-pyridyl |
| O | O | CH₂−CH₂−O−CH₂−CH₂ | 4-pyridyl |
| O | S | −CH₂−CH(CH₂−F)− | 2-pyridyl |
| S | O | −CH₂−CH(CH₂−F)− | 2-pyridyl |
| O | O | −CH₂−CH(CH₂−F)− | 2-pyridyl |
| CH₂ | S | −CH₂−CH(CH₂−F)− | 2-pyridyl |

-continued

| X | R¹ | B | Het |
|---|----|---|-----|
| O | O | -CH₂-CH(CH₃)- | 2-methylpyridine |
| O | O | -CH₂-CH(CH₃)- | 6-methyl-3-(4-methylpiperazin-1-yl)pyridazine |
| O | O | -CH₂-CH(CH₂F)- | 6-methyl-3-(2,6-dimethylmorpholin-4-yl)pyridazine |
| S | O | -CH₂-CH(CH₂F)- | 6-methyl-3-[4-(isopropyl)piperazin-1-yl]pyridazine |
| CH₂ | O | -CH₂-CH(CF₃)- | 6-methyl-3-(2,6-dimethylmorpholin-4-yl)pyridazine |
| O | O | -CH₂-CH(CF₃)- | 6-methyl-3-morpholinopyridazine |
| O | O | -CH₂-CH(CCl₃)- | 6-methyl-3-(2,6-dimethylmorpholin-4-yl)pyridazine |
| S | O | -CH₂-CH(CCl₃)- | 6-methyl-3-morpholinopyridazine |

The benzoylureas include compounds of the formula (V):

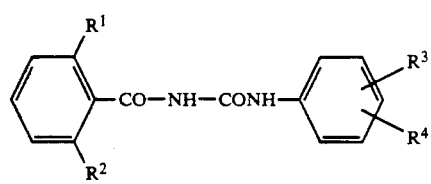

where
R¹ represents halogen,
R² represents hydrogen or halogen,
R³ represents hydrogen, halogen or $C_{1-4}$-alkyl,
R⁴ represents halogen, 1-5-halogeno-$C_{1-4}$-alkyl, $C_{1-4}$-alkoxy, 1-5-halogeno-$C_{1-4}$-alkoxy, $C_{1-4}$-alkylthio, 1-5-halogeno-$C_{1-4}$-alkylthio, phenoxy or pyridyloxy, each of which can be optionally substituted by halogen, $C_{1-4}$-alkyl, 1-5-halogeno-$C_{1-4}$-alkyl, $C_{1-4}$-alkoxy, 1-5-halogeno-$C_{1-4}$-alkoxy, $C_{1-4}$-alkylthio, or 1-5-halogeno-$C_1$-$C_4$-alkylthio.

The following may be mentioned in particular:

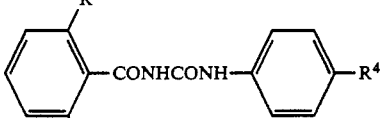

| R¹ | R² | R⁴ |
|----|----|----|
| H | Cl | CF₃ |
| Cl | Cl | CF₃ |

-continued

[Structure: 2,6-disubstituted phenyl-CONHCONH-phenyl-R⁴ with R¹, R²]

| R¹ | R² | R⁴ |
|---|---|---|
| F | F | CF₃ |
| H | F | CF₃ |
| H | Cl | SCF₃ |
| F | F | SCF₃ |
| H | F | SCF₃ |
| H | Cl | OCF₃ |
| F | F | OCF₃ |
| H | F | OCF₃ |
| F | F | O-phenyl-Cl |
| F | F | O-phenyl-CF₃ |
| F | F | O-phenyl-CF₃ |

The triazines include compounds of the formula (VI)

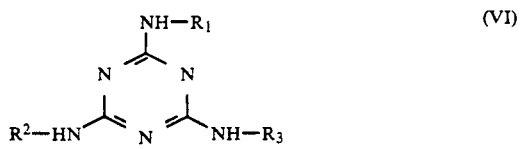

where $R^1$ represents cyclopropyl or isopropyl;

$R^2$ represents hydrogen, halogen, $C_1$-$C_{12}$-alkylcarbonyl, cyclopropylcarbonyl, $C_1$-$C_{12}$-alklcarbamoyl, $C_1$-$C_{12}$-alkylthiocarbamoyl or $C_2$-$C_6$-alkenylcarbamoyl; and $R^3$ represents hydrogen, $C_1$-$C_{12}$-alkyl, cyclopropyl, $C_2$-$C_6$-alkenyl, $C_1$-$C_{12}$-alkylcarbonyl, cyclopropylcarbonyl, $C_1$-$C_{12}$-alkylcarbamoyl, $C_1$-$C_{12}$-alkylthiocarbamoyl or $C_2$-$C_6$-alkenylcarbamoyl, and their acid addition salts which are non-toxic to warmblooded species.

The following may be mentioned in particular:

| R₁ | R₂ | R₃ |
|---|---|---|
| Cyclopropyl | H | H |
| Cyclopropyl | H | CH₃ |
| Cyclopropyl | H | C₂H₅ |
| Cyclopropyl | H | C₃H₇-n |
| Cyclopropyl | H | C₄H₉-n |
| Cyclopropyl | H | C₅H₁₁-n |
| Cyclopropyl | H | C₆H₁₃-n |
| Cyclopropyl | H | C₅H₁₅-n |
| Cyclopropyl | H | C₈H₁₇-n |
| Cyclopropyl | H | C₁₂H₂₅-n |
| Cyclopropyl | H | CH₂—C₄H₉-t |
| Cyclopropyl | H | CH₂CH(CH₃)C₂H₅ |
| Cyclopropyl | H | CH₂CH=CH₂ |
| Cyclopropyl | Cl | C₂H₅ |
| Cyclopropyl | Cl | C₆H₁₃-n |
| Cyclopropyl | Cl | C₈H₁₇-n |
| Cyclopropyl | Cl | C₁₂H₂₅-n |
| Cyclopropyl | H | Cyclopropyl |
| Cyclopropyl | H | COCH₃ |
| Cyclopropyl | H | COCH₃.HCl |
| Cyclopropyl | H | COC₂H₅.HCl |
| Cyclopropyl | H | COC₂H₅ |
| Cyclopropyl | H | COC₃H₇-n |
| Cyclopropyl | H | COC₃H₇-i |
| Cyclopropyl | H | COC₄H₉-t.HCl |
| Cyclopropyl | H | COC₄H₉-n |
| Cyclopropyl | H | COC₆H₁₃-n |
| Cyclopropyl | H | COC₁₁—H₂₃-n |
| Cyclopropyl | COCH₃ | COC₂H₅ |
| Cyclopropyl | COC₃H₇-n | COC₆H₁₃-n |
| Cyclopropyl | COCH₃ | COC₃H₇-n |
| Cyclopropyl | COC₂H₅ | COC₃H₇-n |
| Cyclopropyl | H | COCyclopropyl |
| Cyclopropyl | COCylclopropyl | COCyclopropyl |
| Cyclopropyl | COCH₃ | COCH₃ |
| Isopropyl | H | H |
| Isopropyl | H | COCH₃ |
| Isopropyl | H | COC₃H₇-n |
| Cyclopropyl | H | CONHCH₃ |
| Cyclopropyl | H | CONHC₃H₇-i |
| Cyclopropyl | CONHCH₃ | CONHCH₃ |
| Cyclopropyl | H | CSNHCH₃ |
| Cyclopropyl | H | CONHCH₂CH=CH₂ |
| Cyclopropyl | CONHCH₂CH=CH₂ | CONHCH₂CH=CH₂ |
| Cyclopropyl | CSNHCH₃ | CSNHCH₃ |

The abovementioned substituted diaryl ethers of the formula I must be particularly emphasised.

Insecticides which may be incorporated into the collars according to the invention in addition to the development inhibitors mentioned are: phosphates, such as, for example, fenthion, carbamates such as, for example, propoxur, pyrethroids such as, for example, cyfluthrin or flumethrin.

Substances which can be used for producing the collars according to the invention are polyvinyl resins, polyurethanes, polyacrylates, epoxy resins, cellulose, cellulose derivatives, polyamides and polyesters which are sufficiently compatible with the abovementioned active compounds. The polymers must have sufficiently high strength and flexibility so as not to crack or become brittle when formed into a collar. They must be sufficiently durable so as to be resistant to normal wear and tear. Moreover, the polymers must permit sufficient migration of the active compounds to the surface of the moulding. These properties are met, in particular, by solid polyvinyl resins, that is to say polymers which are formed by polymers of a vinyl double bond.

Examples of typical vinyl resins are polyvinyl halides, such as polyvinyl chloride, polyvinyl chloride/vinyl acetate and polyvinyl fluoride; polyacrylate esters and polymethacrylate esters such as polymethyl acrylate and polymethyl methacrylate; and polyvinylbenzenes such as polystyrene and polyvinyltoluene.

Suitable plasticisers for the production of the collars according to the invention on the basis of polyvinyl resin are those which are customarily used for plasticising solid vinyl resins. The plasticiser to be used depends on the resin and its compatibility with the plasticiser. Examples of suitable plasticisers are esters of phosphoric acid, such as tricresyl phosphate, esters of phthalic acid, such as dimethyl phthalate and dioctyl phthalate, and esters of adipic acid, such as diisobutyl adipate. It is also possible to use other esters, such as the esters of azelaic acid, maleic acid, ricinoleic acid, myristic acid, palmitic acid, oleic acid, sebacic acid, stearic acid and trimellitic acid, and also complex linear polyesters, polymeric plasticisers and epoxidised soybean oils. The amount of plasticiser is approximately 10 to 50% by weight, preferably about 20 to 45% by weight, of the entire composition.

The collars can also contain other components such as stabilisers, spreading agents, lubricants, fillers and colourants, without this changing the basic properties of the composition. Suitable stabilisers are antioxidants and agents which protect the collars from ultraviolet rays and undesired degradation during processing, such as extrusion moulding. Some stabilisers, such as epoxidised soybean oils, also act as secondary plasticisers. Examples of lubricants which can be used are stearates, stearic acid and low-molecular-weight polyethylenes. These components can be used in a concentration of up to approximately 5% by weight of the entire composition.

In the production of the collars according to the invention on a vinyl basis, the various components are mixed in the dry state using known mixing methods, and the mixture is moulded using known extruding or injection-moulding methods.

The choice of the processing method for the production of the collars according to the invention depends technically in principle on the rheological properties of the collar material and the shape of the desired collar. The processing methods can be adjusted to suit the processing technology or the nature of the shaping process. In the case of process technology, the methods can be divided on the basis of the rheological states which the material assumes. Accordingly, pouring, pressing, inject on moulding and coating are suitable for viscous collar materials, and injection moulding, extruding, calendering, rolling and, if appropriate, edging in the case of elastoviscous polymers. Divided according to the nature of shaping, the mouldings according to the invention can be produced by casting, dipping, compression moulding, injection moulding, extruding, calendering, embossing, bending, thermoforming etc.

These processing methods are known and need no further explanation. What has been illustrated above by way of example for polyvinyl resins is also true in principle in the case of other polymers.

Other support materials for the collars according to the invention are polyurethanes. These are prepared in a manner known per se by reacting polyisocyanates with high-molecular compounds which have at least two groups which are reactive towards isocyanates and, if appropriate, with low-molecular chain extenders and/or monofunctional chain terminators.

They are prepared by methods known in principle (for example compare European Offenlegungsschrift (European Published Specification) 50,782, German Offenlegungsschrift (German Published Specification) 2,715,596 and the references cited therein).

The concentrations of the active compounds in the support polymers are 0.05-20% by weight. Preferred concentrations are 0,1-5% by weight. A concentration of active compound of around approximately 1 per cent by weight is particularly preferred.

In the examples below the following active compounds are used:
Pyriproxyfen: 2-[1-methyl-2-(4-phenoxyphenoxy)-ethoxy]-pyridine Triflumuron=1-(2-chlorobenzoyl)-3-(4-trifluoromethoxyphenyl)-urea
Propoxur=2-isopropoxyphenyl-N-methyl carbamate
Cyfluthrin: Cyano-(4-fluoro-3-phenoxyphenyl)-methyl-3-(2,2-dichlorovinyl)-2,2-dimethyl-cylcopropane carboxylate

EXAMPLE A

The test is carried out using PVC collars which contain by weight of the compound pyriproxyfen of the formula

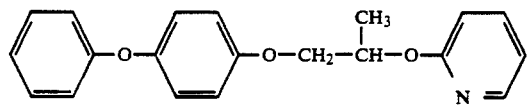

Tiled pens of approx. 170×270 cm are covered with carpet (3.4 m²), the area of the feed bowls and litter tray remaining uncovered, and 2 cats wearing the collars to be tested are placed in the pens. After 1 week, the carpets are removed from the pens and in each case 20 test discs of 80 mm diameter are cut out. The discs should be distributed on the carpet as uniformly as possible.

The carpet discs are scattered with a spatula-tipful of blood meal (specification: blood meal (powder) for feed purposes; manufactured by Ssniff), and infested with eggs or L1 larvae of the flea species to be tested. They are kept in an incubation cabinet at 25° C./80% relative humidity. The development of the flea larvae is checked every three days. The dishes in which larva development takes place are sealed tightly after about 14 days using Parafilm or Tesafilm so as to prevent the adult fleas from escaping. The test is concluded one week after the fleas in the untreated controls have hatched. The dishes in which the development of adult fleas took place are kept for 24 hours in a freezer at −15°-18° C. and are then evaluated. Even though larvae hatch from the eggs, no adult fleas develop, even after 16 weeks.

PRODUCTION EXAMPLES

Examples of Polyurethane Collars

The collars are produced continuously by the casting process with the aid of a belt conveyor system. The polyether, the active compound or active compound combination, the colouring paste, the zeolite paste, the spreading agent and 1,4-butanediol are mixed together in a heatable vessel and heated to 60° C. The catalyst (dibutyl tin dilaurate) is then added.

The resulting mixture is component A, which is mixed with component B in a weight ratio of 1:1 using a mixing apparatus. The mixing head is attached to an oscillating traversing device. The reaction mixture flows continuously from the mixing head on to a supporting material (e.g. coating on a plastic belt). The reaction mixture begins to react 30 secs after issuing from the mixing head and hardens after about 60 secs.

The web of material then passes through a cooling zone. The product has solidified to such an extent that it can be passed to the cutting device via a system of slowly rotating V-belts.

EXAMPLE 1

Component A:

-continued

| | |
|---|---|
| Trihydroxypolyether (m.w. 4,800) | 41.18 parts by weight |
| 1,4-butanediol (crosslinking agent) | 5.00 parts by weight |
| Pigment (iron oxide) | 0.50 parts by weight |
| Zeolite paste (1:1 in castor oil) | 0.50 parts by weight |
| Triflumuron | 10.00 parts by weight |
| Hexyl laurate (spreading agent) | 18.00 parts by weight |
| Dibutyl tin dilaurate | 0.02 parts by weight |
| Component B: | |
| Tripropylene-glycol-modified 4,4'-diisocyanatodiphenylmethane, isocyanate content: 23% by weight | 24.80 parts by weight |

EXAMPLE 2

| | |
|---|---|
| Component A: | |
| Trihydroxypolyether (m.w. 4,800) | 39.063 parts by weight |
| 1,4-butanediol | 5.000 parts by weight |
| Pigment (iron oxide) | 0.500 parts by weight |
| Zeolite paste (1:1 in castor oil) | 0.500 parts by weight |
| Propoxur | 8.00 parts by weight |
| Pyriproxyfen | 1.00 parts by weight |
| Isopropyl myristate (spreading agent) | 22.00 parts by weight |
| Dibutyl tin dilaurate | 0.037 parts by weight |
| Component B: | |
| Tripropylene-glycol-modified 4,4'-diisocyanatodiphenylmethane, isocyanate content: 23% by weight | 23.90 parts by weight |

EXAMPLE 3

| | |
|---|---|
| Component A: | |
| Trihydroxypolyether (m.w. 4,800) | 51.48 parts by weight |
| 1,4-butanediol | 5.00 parts by weight |
| Pyriproxyfen | 1.50 parts by weight |
| Cyfluthrin | 7.50 parts by weight |
| Pigment (iron oxide) | 0.50 parts by weight |
| Zeolite paste (1:1 castor oil) | 0.50 parts by weight |
| Ester of a branched fatty acid with saturated fatty alcohols/$C_{12}$-$C_{18}$ (spreading agent) | 8.00 parts by weight |
| Dibutyl tin dilaurate | 0.02 parts by weight |
| Component B: | |
| Tripropylene-glycol-modified 4,4'-diisocyanatodiphenylmethane, isocyanate content: 23% by weight | 25.50 parts by weight |

EXAMPLES OF PVC COLLARS

The active compound, the colourant and the PVC homopolymer are initially fed into a high-speed mixer and mixed thoroughly. The speed of the mixer is increased and the temperature raised to 60° C.

Then diisobutyl adipate, dioctyl phthalate and the wetting agent are added and the mixture is mixed further until the temperature has again reached 60° C.

The mixture is slowly stirred further until it is dry and powdery in appearance.

Then stearic acid is added.

The mixture is then cooled rapidly with stirring.

This mixture is processed in an injection-moulding machine to form collars of the appropriate shape.

EXAMPLE 4

| | |
|---|---|
| Pyriproxyfen | 0.70 parts by weight |
| Diisobutyl adipate | 23.25 parts by weight |
| Dioctyl phthalate | 10.03 parts by weight |
| Epoxidised soybean oil (wetting agent) | 2.54 parts by weight |
| Stearic acid | 0.88 parts by weight |
| Iron oxide pigment | 0.14 parts by weight |
| PVC homopolymer | 62.46 parts by weight |

EXAMPLE 5

| | |
|---|---|
| Pyriproxyfen | 0.20 parts by weight |
| Propoxur | 10.00 parts by weight |
| Diisobutyl adipate | 17.25 parts by weight |
| Dioctyl phthalate | 6.03 parts by weight |
| Epoxidised soybean oil | 2.54 parts by weight |
| Stearic acid | 0.88 parts by weight |
| PVC homopolymer | 62.96 parts by weight |

EXAMPLE 6

| | |
|---|---|
| Pyriproxyfen | 0.50 parts by weight |
| Cyfluthrin | 10.00 parts by weight |
| Stearic acid | 0.88 parts by weight |
| Iron oxide pigment | 0.10 parts by weight |
| PVC homopolymer | 60.52 parts by weight |
| Tributyl citrate | 18.00 parts by weight |
| Triacetin | 10.00 parts by weight |

We claim:

1. A method of combating fleas on and in the surroundings of a domestic animal which comprises placing on said animal a collar comprising a layer exposed to the atmosphere containing an insect-development-inhibiting active compound of the formula

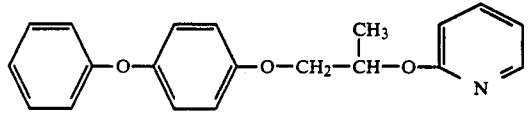

plus an insecticide active against adult fleas selected from the group consisting of an organophosphate, carbamate or pyrethroid, wherein the insect-development-inhibiting compound is present in said layer in about 0.7 to 10.5 parts by weight, wherein the collar is produced by mixing the polymer, the insect-development-inhibiting active compound and the insecticide and molding the mixture to form the exposed surface of the collar, wherein the polymer is selected form the group consisting of polyvinyl halides, polyacrylate or polymethacrylate esters, polyvinylbenzenes, and polyurethanes.

2. A method according to claim 1, wherein the insecticide is a carbamate.

3. A method according to claim 1, wherein the carbamate is propoxur.

4. A method according to claim 1, wherein the insecticide is an organophosphate.

5. A method according to claim 1, wherein the insecticide is a pyrethroid.

6. A method according to claim 1, wherein the insecticide is cyfluthrin.

7. A method according to claim 1, wherein the insecticide is flumethrin.

* * * * *

UNITED STATES PATENT AND TRADEMARK OFFICE
CERTIFICATE OF CORRECTION

PATENT NO : 5,266,324
DATED : November 30, 1993
INVENTOR(S) : Wilhelm Stendel, et al.

It is certified that error appears in the above-identified patent and that said Letters Patent are hereby corrected as shown below:

Column 28, line 53,   cancel "form" and substitute --from--.

Signed and Sealed this

Fourteenth Day of December, 1999

Attest:

Q. TODD DICKINSON

*Attesting Officer*   *Acting Commissioner of Patents and Trademarks*